US008913251B2

(12) United States Patent
Tin

(10) Patent No.: US 8,913,251 B2
(45) Date of Patent: Dec. 16, 2014

(54) ESTIMATING MATERIAL PROPERTIES USING SPECKLE STATISTICS

(75) Inventor: Siu-Kei Tin, Milpitas, CA (US)

(73) Assignee: Canon Kabushiki Kaisha, Tokyo (JP)

(*) Notice: Subject to any disclaimer, the term of this patent is extended or adjusted under 35 U.S.C. 154(b) by 164 days.

(21) Appl. No.: 13/595,058

(22) Filed: Aug. 27, 2012

(65) Prior Publication Data

US 2014/0055792 A1 Feb. 27, 2014

(51) Int. Cl.
*G01B 11/30* (2006.01)
*G01B 11/02* (2006.01)
*G01N 21/00* (2006.01)
*G01B 9/02* (2006.01)
*G01B 11/16* (2006.01)

(52) U.S. Cl.
CPC .......... *G01B 9/02094* (2013.01); *G01B 11/162* (2013.01)
USPC .......... 356/600; 356/237.2; 356/496

(58) Field of Classification Search
CPC .......... G01B 9/02094; G01B 11/162
USPC .......... 356/496, 511–512, 600, 237.1–237.5
See application file for complete search history.

(56) References Cited

U.S. PATENT DOCUMENTS

| | | | |
|---|---|---|---|
| 4,145,140 A | 3/1979 | Fujii | |
| 4,682,892 A * | 7/1987 | Chawla | 356/458 |
| 5,311,286 A | 5/1994 | Pike | |
| 5,426,506 A * | 6/1995 | Ellingson et al. | 356/369 |
| 5,689,332 A * | 11/1997 | Ellingson et al. | 356/237.1 |
| 6,847,449 B2 | 1/2005 | Bashkansky et al. | |
| 7,728,295 B2 | 6/2010 | Miles et al. | |
| 2004/0046959 A1* | 3/2004 | Meeks et al. | 356/369 |
| 2008/0123106 A1* | 5/2008 | Zeng et al. | 356/600 |
| 2012/0130253 A1* | 5/2012 | Nadkarni et al. | 600/476 |

OTHER PUBLICATIONS

Tchvialeva, et al., "Skin roughness assessment", in New Developments in Biomedical Engineering, 2010.

* cited by examiner

*Primary Examiner* — Kara E Geisel
*Assistant Examiner* — Dominic J Bologna
(74) *Attorney, Agent, or Firm* — Fitzpatrick, Cella, Harper & Scinto

(57) ABSTRACT

A surface roughness value and a sub-surface scattering property of a material are estimated. The material is illuminated with a light beam with controlled coherence properties at multiple incident angles. Multiple speckle patterns are recorded, each speckle pattern being recorded for a respective one of the multiple incident angles. Both of a surface roughness value and a sub-surface scattering property of the material are estimated by calculations using the multiple speckle patterns and the incident angle for each such speckle pattern.

17 Claims, 6 Drawing Sheets

US 8,913,251 B2

ESTIMATING MATERIAL PROPERTIES USING SPECKLE STATISTICS

FIELD

The present disclosure relates to estimating material properties using speckle statistics.

BACKGROUND

Estimation of material properties can be used in material classification, discrimination and identification. Optical methods of estimation generally have the benefit of not requiring physical contact with a material sample and avoiding potential damage to the sample. Examples of material properties that can be estimated by optical measurement of scattering of light include surface roughness, spectral reflectance, bidirectional reflectance distribution function (BRDF), bidirectional surface scattering reflectance distribution function (BSSRDF) and the like. The scattering of light can be due to surface microstructure (in the case of surface roughness) or sub-surface microstructure (in the case of sub-surface scattering described by the BSSRDF).

In the field of measuring surface roughness of a material, it is known that there is a correlation between surface roughness and intensity statistics of a speckle pattern. A speckle pattern typically results from interference of light waves scattered by a material when illuminated by a controlled coherent light source such as a laser. The nature of the speckle pattern depends in part on surface roughness, and it is often possible to estimate surface roughness by deriving a speckle statistic from the speckle pattern.

SUMMARY

Attempts to use laser speckle to estimate material properties have generally been limited to estimation of surface roughness, which is only one aspect of the material. In terms of material classification, discrimination and identification, other aspects such as sub-surface scattering properties are equally important.

In addition, attempts to correlate speckle statistics with surface roughness have generally been unsatisfactory due to ignoring the effect of sub-surface scattering, which can significantly alter the optical paths of light waves in translucent or semi-transparent materials. Ignoring sub-surface scattering in the estimation of surface roughness results in an "apparent surface roughness", which can be significantly different from the true surface roughness.

The foregoing situation is addressed by estimating both of a surface roughness value and a sub-surface scattering property of a material using multiple speckle patterns obtained from illuminating the material at multiple incident angles.

Thus, in an example embodiment described herein, a surface roughness value and a sub-surface scattering property of a material are estimated. The material is illuminated with a light beam with controlled coherence properties at multiple incident angles. Multiple speckle patterns are recorded, each speckle pattern being recorded for a respective one of the multiple incident angles. Both of a surface roughness value and a sub-surface scattering property of the material are estimated by calculations using the multiple speckle patterns and the incident angle for each such speckle pattern.

By using multiple speckle patterns obtained from illuminating the material at multiple incident angles, it is ordinarily possible to estimate the true surface roughness and sub-surface scattering property at the same time.

In other aspects, the surface roughness and sub-surface scattering are related using a model. The model defines relatedness amongst the apparent surface roughness, the true surface roughness, the sub-surface scattering property, and the incident angle. A numeric value for the apparent surface roughness is determined for each of the multiple speckle patterns by calculating a speckle statistic for each such speckle pattern. The numeric values are fitted to the model. Both of the surface roughness and the sub-surface scattering property are estimated from the fitted model.

In still other aspects, a material is illuminated at multiple incident angles by a multi-angle illumination system including a scanning mirror that deflects the light beam to a curved mirror, and the curved mirror reflects the light beam to the material at different incident angles depending on the position of the scanning mirror.

This brief summary has been provided so that the nature of this disclosure may be understood quickly. A more complete understanding can be obtained by reference to the following detailed description and to the attached drawings.

DETAILED DESCRIPTION

Figure 1A:
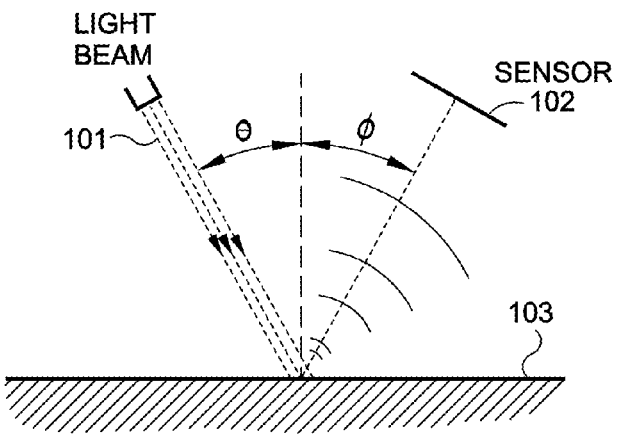
FIGS. 1A, 1B and 1C are views for explaining a material estimating device based on measurement of speckle patterns according to an example embodiment.
Figure 1B:
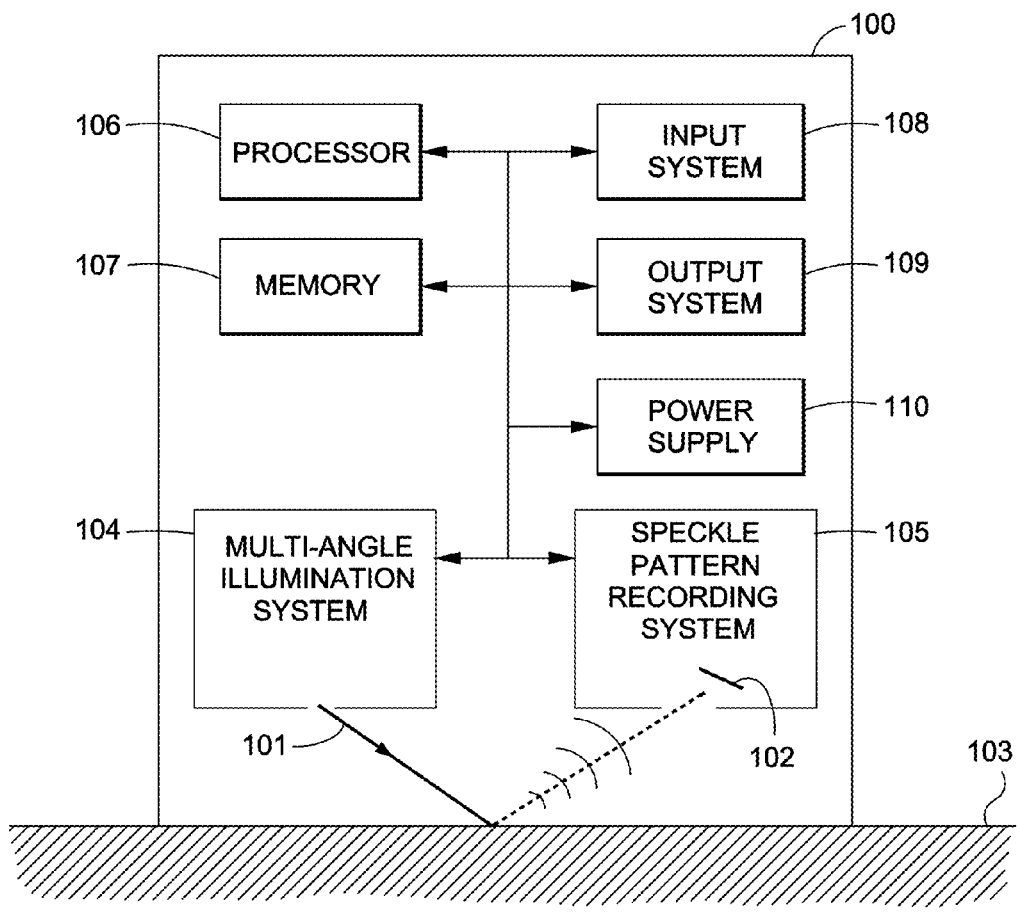
Figure 1C:
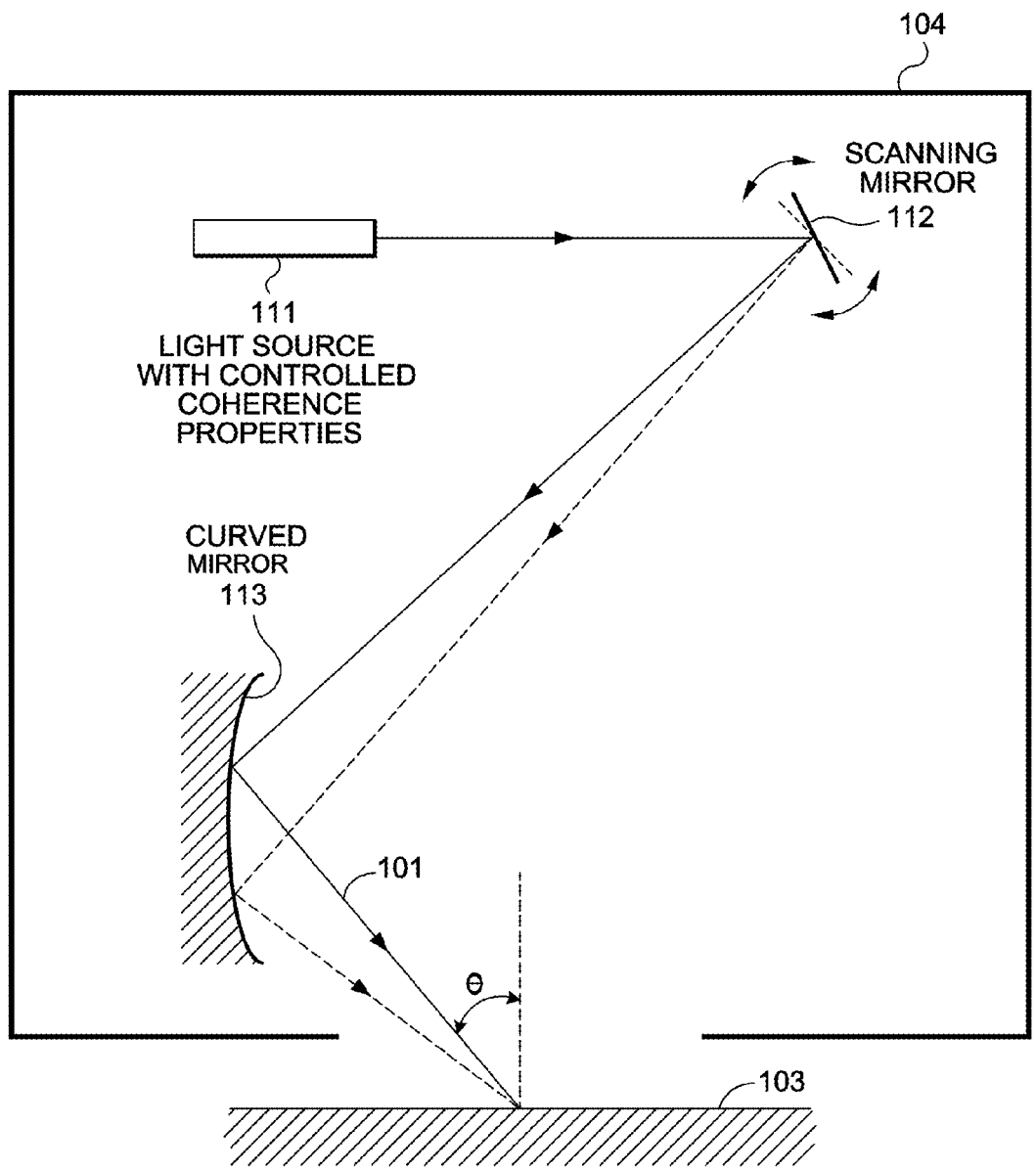

FIGS. 1A, 1B and 1C are views for explaining a material estimating device based on measurement of speckle patterns according to an example embodiment.

In particular, FIGS. 1A, 1B and 1C are views for explaining a device which illuminates a material from multiple incident angles, and records resultant speckle patterns formed on one or more sensors.

In the simplified view shown in FIG. 1A, a light beam 101 with controlled coherence properties illuminates a material 103 at multiple incident angles, of which one angle "θ" is illustrated. Sensor 102 records multiple speckle patterns, each speckle pattern being recorded for a respective one of the multiple incident angles. Both of a surface roughness value and a sub-surface scattering property of the material 103 are estimated by calculations using the multiple speckle patterns and the incident angle for each such speckle pattern, as discussed more fully below. Material 103 may comprise, for example, a translucent material such as skin tissue, or a material to be sorted such as a recyclable material.

As shown in FIG. 1A, multiple illuminations are performed with different incident angles θ, and multiple speckle patterns are recorded at observation angle φ that may change in dependence on the respective incident angle θ. In that regard, using different incident angles allows multiple material properties, such as surface roughness and sub-surface scattering, to be estimated simultaneously, as discussed more fully below.

FIG. 1B is a simplified view of material estimating device 100 for estimating material properties of the material 103 as shown in FIG. 1A. In that regard, material estimating device 100 is shown in FIG. 1B as a device which is placed on or near to material 103, but it should be understood that material estimating device 100 might be embodied in other arrangements and with other positioning relative to material 103. For example, material estimating device 100 could be arranged in other housings or devices which include a laser emitter and sensor as shown in FIG. 1A. In addition, the elements of FIG. 1A or FIG. 1B could be embodied in separate devices or across multiple devices in a system. For example, light beam 101 and sensor 102 could be embodied in two or more devices.

As shown in FIG. 1B, material estimating device 100 includes light beam 101, sensor 102, multi-angle illumination system 104, speckle pattern recording system 105, processor 106, memory 107, input system 108, output system 109 and power supply 110.

Light beam 101 is a light beam with controlled coherence properties. For example, light beam 101 might comprise a monochromatic laser beam.

Sensor 102 is a sensor for recording the speckle pattern which results from interference of light waves scattered by material 103 when illuminated by light beam 101 having controlled coherence properties.

Multi-angle illumination system 104 is a system for driving light beam 101 to illuminate material 103 from multiple incident angles. In that regard, FIG. 1C shows an embodiment of the multi-angle illumination system 104 consisting of a scanning mirror 112, such as one based on a galvanometer, that deflects the light beam 101 from a light source with controlled coherence properties 111 to the curved mirror 113. The light beam in turn is reflected by the curved mirror 113 to the same spot on the material 103 but at different incident angles depending on the position of the scanning mirror. Other embodiments of multi-angle illumination system 104 might comprise, for example, one or more stepper motors and associated parts for physically moving light source with controlled coherence properties 111 so as to produce light beam 101 at different incident angles, or might comprise multiple ones of light source with controlled coherence properties 111 set to produce multiple ones of light beam 101 at different angles.

Speckle pattern recording system 105 is a system for recording the speckle patterns respectively created by driving light beam 101 to illuminate material 103 from the multiple incident angles. In that regard, speckle pattern recording system 105 may be based on a free space imaging geometry or a configuration involving use of imaging lens(es). The sensor 102 may be set at a fixed observation angle $\phi$, or its position may be changed by a stepper motor to allow variable observation angles $\phi$ with respect to different incident angles $\theta$.

Processor 106 a computer processor such as a single core or multi-core central processing unit (CPU) or micro-processing unit (MPU), which is constructed to realize functionality according to the disclosure. Processor 106 might comprise multiple computer processors which are constructed to work together. Processor 106 communicates with the elements of material estimating device 100 to control the elements to perform required functionality or to obtain required data. For example, processor 106 may control multi-angle illumination system 104 to illuminate material 103 from different angles, and may control speckle pattern recording system 105 to record speckle patterns from the different incident angles.

Memory 107 stores constants, computer-executable programs, and the like for operation of processor 106, including programs for execution of various flowcharts. Memory 107 may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like.

Figure 3:
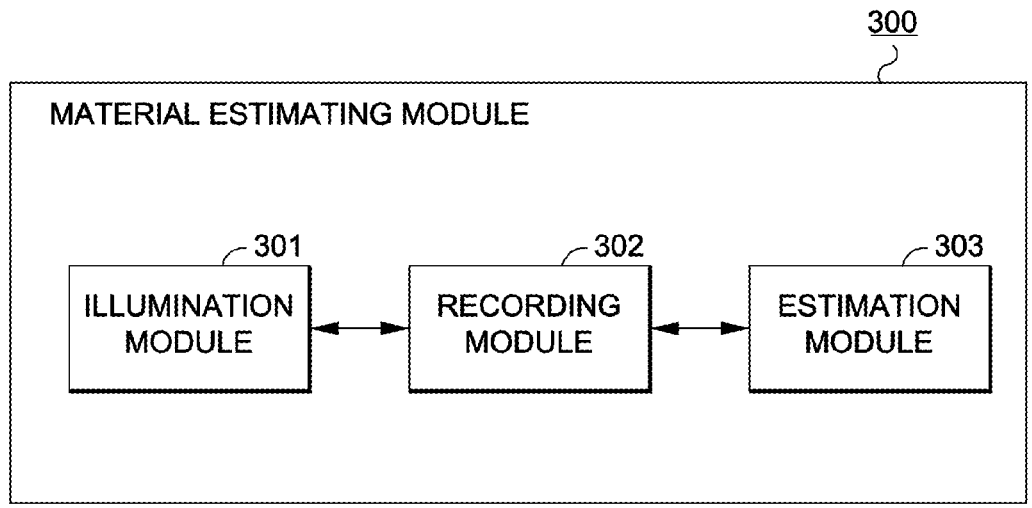
FIG. 3 is a view for explaining a material estimating module according to one example embodiment.

Memory 107 may retrievably store thereon material estimating module 300 as described herein and shown in FIG. 3. According to this example embodiment, the material estimating module 300 includes at least an illumination module 301 for illuminating the material with a light beam with controlled coherence properties at multiple incident angles, a recording module 302 for recording multiple speckle patterns, each speckle pattern being recorded for a respective one of the multiple incident angles, and an estimation module 303 for estimating both of a surface roughness value and a sub-surface scattering property of the material by calculations using the multiple speckle patterns and the incident angle for each such speckle pattern.

Input system 108 inputs data such as settings or control parameters for operation of material estimating device 100. For example, in some example embodiments, it might be useful to input precise control parameters from an external processing device such as a computer. Accordingly, input system 108 may include a connection and associated elements for communicating with other devices.

Output system 109 provides output of data obtained or produced from material estimating device 100, either to a user, e.g., via a display in output system 109 or via a connection to output data to an external device.

Power supply 110 is a primary power source such as an alkaline battery or a lithium battery, a secondary battery such as a NiCd battery, a NiMH battery or a Li battery, or the like for providing power to material estimating device 100.

In FIG. 1B, material estimating device 100 is shown as a standalone device, but other embodiments might involve multi-angle illumination system 104 and/or speckle pattern recording system 105 in a first housing coupled to remaining components in a second housing, such as by unshown wireless or wired interfaces to a computer.

Figure 2:
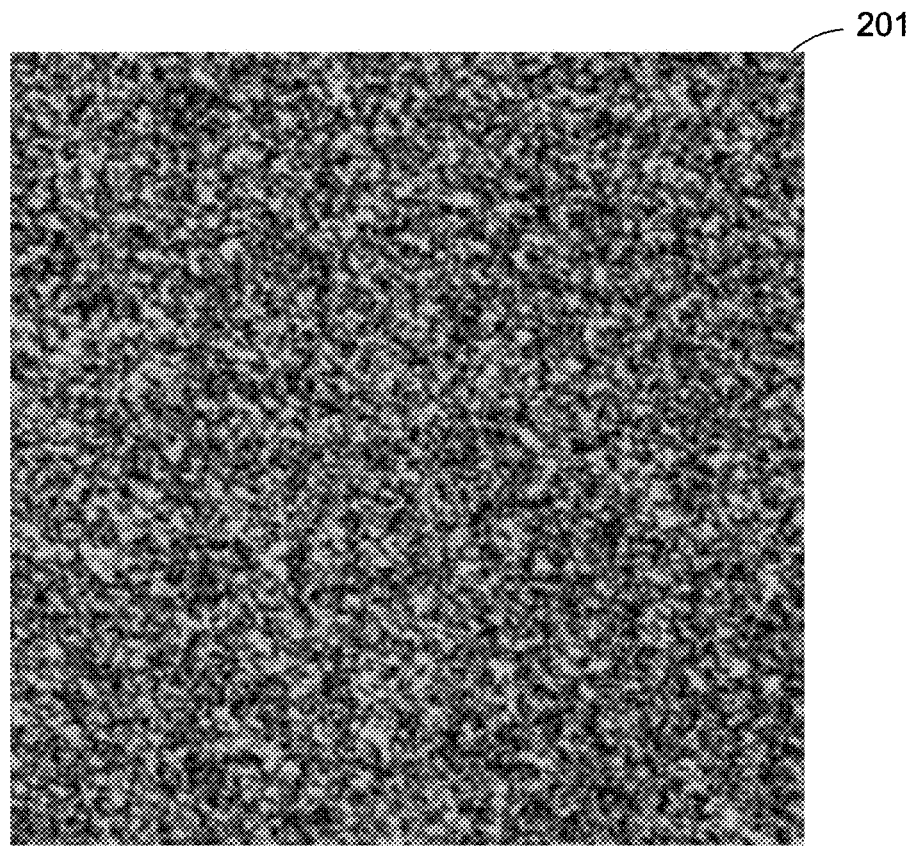
FIG. 2 is a view for explaining a speckle pattern according to an example embodiment.

FIG. 2 is a view for explaining a speckle pattern according to an example embodiment.

In that regard, speckle patterns are formed when an object is illuminated by a coherent light such as a laser. An exemplary speckle pattern is shown in FIG. 2. The pattern is caused in part by the surface microstructure of the material, but is also caused by the sub-surface microstructure of the illuminated material, and the speckle pattern can be used to determine or estimate these properties of the illuminated material. In that regard, the speckle pattern may appear to be random, but the statistical properties can be correlated to the surface microstructure (e.g., surface roughness) and sub-surface microstructure (e.g., sub-surface scattering) of the illuminated material.

The light used for the illumination must have some degree of coherence, because the speckle pattern is caused by the interference of coherent light waves with the material. Coherence may include spatial coherence (e.g., light waves remaining correlated over a long distance, possibly averaged over time) and temporal coherence (e.g., light waves remaining correlated over long time). One example of a light source with spatial and temporal coherence is a monochromatic laser. In some embodiments, temporal coherence may not be required.

According to the disclosure, both surface roughness and sub-surface scattering are estimated.

In that regard, surface roughness refers to the variation of heights of the surface profile of the material. Nevertheless, according to the disclosure, it is ordinarily not necessary to measure the surface profile of the material, which might require contact and/or destructive measurement of the surface of the material. Rather, statistics such as the standard deviation of the surface heights are obtained and correlated with properties of the material. Put another way, a measure of surface roughness based on the statistical distribution of surface profile heights is used, rather than trying to measure the surface profile directly.

For example, one measure of surface roughness is the root mean square (RMS) surface roughness, i.e., the standard deviation the statistical distribution of the surface heights $\sigma_h$, also denoted $R_q$. Other measures of surface roughness may be used, such as $R_a$, which is the average of the absolute value of deviations from the mean surface height.

Meanwhile, sub-surface scattering refers to an effect caused when light hits a translucent material. In that regard, most materials (e.g., skin, marble, etc.) are translucent to some extent. According to the disclosure, sub-surface scattering is treated as a property of the material being illuminated, and can be modeled using certain parameters. The parameters may include general light transport parameters such as an absorption coefficient, a scattering coefficient, an extinction coefficient, a reduced extinction coefficient, an effective extinction coefficient, an albedo parameter, a relative index of refraction, a mean cosine of the scattering angle, a phase function or other parameters, or may include application-specific parameters such as a melanin concentration, a hemoglobin concentration, a melanin type blend parameter, an oiliness parameter or other parameters in an optical model of skin. In that regard, these parameters are not necessarily independent of each other.

According to the disclosure, it may not be necessary to determine all parameters of the sub-surface scattering individually. In fact, due to the number of parameters that affect sub-surface scattering, determining all such parameters may be impractical. Rather, selected parameters may be estimated individually or in combination, which can then be used to classify, discriminate and/or identify the material, as discussed in more detail below.

FIG. 3 is a view for explaining a material estimating module according to one example embodiment. Material estimating module 300 comprises computer-executable process steps stored on a non-transitory computer-readable storage medium, such as memory 107. More or less modules may be used, and other architectures are possible.

As shown in FIG. 3, material estimating module 300 includes at least an illumination module 301 for illuminating the material with a light beam with controlled coherence properties at multiple incident angles. To that end, illumination module 301 may, for example, be executed by processor 106 in order to drive multi-angle illumination system 104 and light beam(s) 101. A recording module 302 is for recording multiple speckle patterns, each speckle pattern being recorded for a respective one of the multiple incident angles. Thus, recording module 302 may, for example, be executed by processor 106 in order to drive speckle pattern recording system 105 and sensor(s) 102. Estimation module 303 is for estimating both of a surface roughness value and a sub-surface scattering property of the material by calculations using the multiple speckle patterns and the incident angle for each such speckle pattern, as discussed in more detail below.

Figure 4:
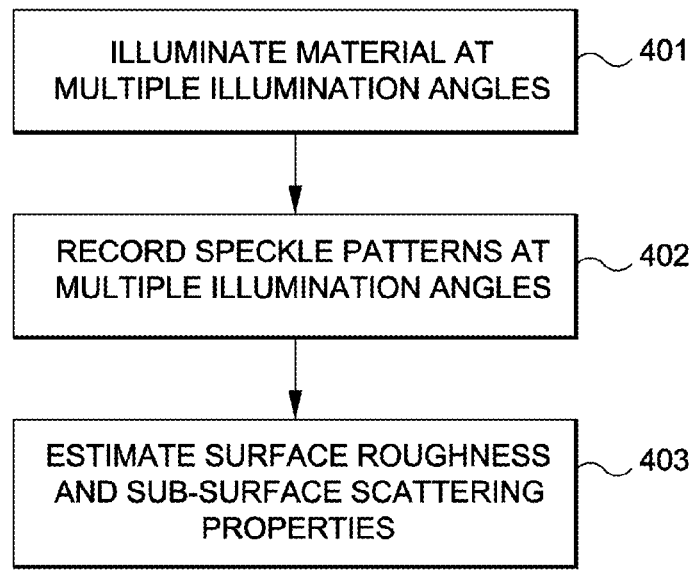
FIG. 4 is a flowchart for explaining processing in the material estimating device shown in FIGS. 1A, 1B and 1C according to an example embodiment.

FIG. 4 is a flowchart for explaining processing in the material estimating device shown in FIGS. 1A, 1B and 1C according to an example embodiment.

Briefly, in FIG. 4, a surface roughness value and a sub-surface scattering property of a material are estimated. The material is illuminated with a light beam with controlled coherence properties at multiple incident angles. Multiple speckle patterns are recorded, each speckle pattern being recorded for a respective one of the multiple incident angles. Both of a surface roughness value and a sub-surface scattering property of the material are estimated by calculations using the multiple speckle patterns and the incident angle for each such speckle pattern.

In more detail, in step 401, the material is illuminated with a light beam with controlled coherence properties at multiple incident angles. For example, multi-angle illumination system 104 may be driven to generate light beam 101 at a different incident angle at a time, using an optical arrangement such as shown in FIG. 1C.

In step 402, the speckle patterns caused by the illumination from the different incident angles are recorded. For example, the speckle patterns can be recorded by sensor 102 and/or speckle pattern recording system 105 depending on the embodiment. The observation angle $\phi$ may be set at each recording of speckle patterns. For example, the observation angle $\phi$ may be set to correspond to the incident angle, e.g., $\phi=\theta$. In another example, the observation angle $\phi$ may be set to be at a constant angle, e.g., $\phi=\phi_0$, where $\phi_0$ is a constant that is used for all recordings of speckle patterns.

In step 403, there is an estimation of both a surface roughness and also a sub-surface scattering property.

In particular, although speckle patterns may appear to be random, various statistics can be calculated that can be correlated to the properties of the material. For example, speckle contrast C is a first order statistic defined as:

$$C = \frac{\sigma_I}{\langle I \rangle}, \tag{1}$$

where I is the speckle intensity, $\langle I \rangle$ is the spatial average, and $\sigma_I$ is the standard deviation.

Figure 5:
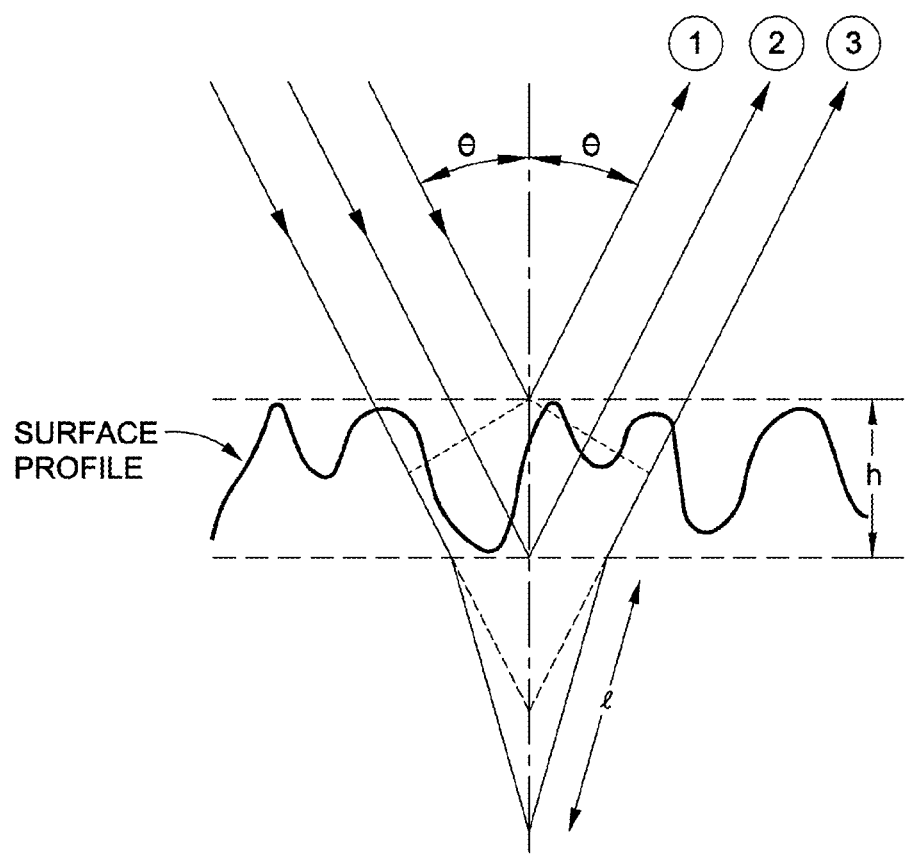
FIG. 5 is a view for explaining light transport at a rough and translucent surface according to an example embodiment.

In that regard, the speckle contrast can be related to surface roughness. FIG. 5 is a figure for explaining the modeling of surface roughness and apparent surface roughness. More specifically, the surface roughness is typically modeled as a standard deviation $\sigma_h$, or RMS value of the deviations of surface heights h from the mean surface height, as discussed above. Referring to FIG. 5, where the observation angle $\phi$ is set to depend on the incident angle $\theta$ such that $\phi=\theta$, the surface profile is illustrative of a magnified view of the surface microstructure. Also illustrated is the surface profile height h, which can be considered a function of the location on the surface, or alternatively, as a random variable with a surface height distribution. Path (1) illustrates propagation of a light wave scattered at a reference surface height, which is thought of having a surface height h of zero. Consider an adjacent light wave scattered at surface height h, with propagation illustrated by path (2). The path difference between these two light waves is given by:

$$\Delta p = 2h \cos \theta \quad (2)$$

The path difference causes a corresponding phase difference between these adjacent waves, resulting in an interference pattern that is the speckle pattern. Since h is a random variable, the interference pattern appears to be random. If there is no sub-surface scattering effect, the path/phase difference given by Equation 2 accounts for the whole speckle pattern formation.

If there is sub-surface scattering, then a light wave may undergo further scattering under the surface. An exemplary propagation path is illustrated in path (3), which shows a single scattering within the material. Depending on the properties of the material such as the magnitude of the scattering coefficient or absorption coefficient, multiple scattering is possible. For path (3) shown in FIG. 5, the assumptions of single scattering and symmetry of incident and observation positions imply that path (3) must be symmetric about the surface normal direction. Path (3) is characterized by an additional random variable f, the free path, or the distance between successive scatterings by the sub-surface microstructure. The path difference between path (1) and path (3) is given by:

$$\Delta p = 2h \cos \theta + 2l/\eta, \quad (3)$$

where, in addition, η is the relative refractive index of the material. Equation 3 shows the combined effect of surface roughness and sub-surface scattering on the path difference between two adjacent light waves, which causes a corresponding phase difference and in turn the formation of a speckle pattern with a speckle contrast statistic incorporating the effect of both random variables h and l.

As explained above, the surface roughness is typically modeled by the root mean square (RMS) surface roughness $\sigma_h$. The RMS surface roughness in turn is typically estimated by using the correlation between the RMS surface roughness and the speckle contrast. However, it is clear from the above consideration that the speckle contrast, which is derived from the speckle pattern, is the result of the overall path/phase difference between adjacent light waves, given by Equation 3. As a result, the true RMS surface roughness $\sigma_h$ is not directly correlated with the speckle contrast. Instead, an "apparent RMS surface roughness" is correlated with the speckle contrast.

Figure 6:
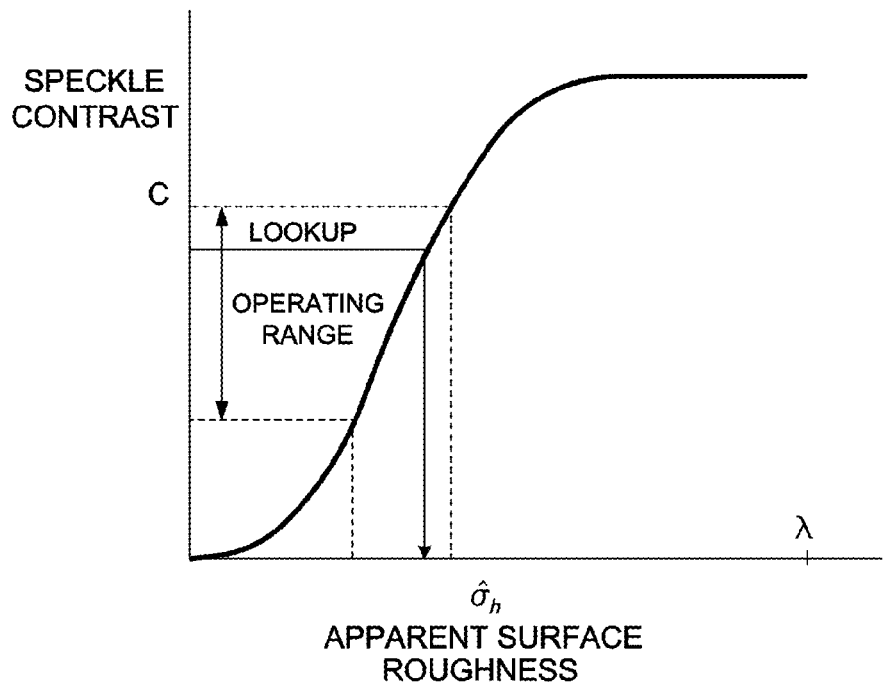
FIG. 6 is a view for explaining a relationship between apparent RMS surface roughness and speckle contrast according to an example embodiment.

FIG. 6 is a view for explaining a relationship between the apparent RMS surface roughness and speckle contrast. FIG. 6 shows a typical relationship for speckle contrast arising from a monochromatic coherent light source, such as a monochromatic laser. As can be seen from FIG. 6, the apparent RMS surface roughness has a one-one correspondence with speckle contrast over a certain range of speckle contrast and apparent RMS surface roughness, e.g., over a range of surface roughness that is substantially away from the magnitude of length represented by the wavelength λ of the monochromatic light source. Other types of light source with controlled coherence properties, such as a polychromatic light source, may have a different relationship, but are applicable as long as an operating range exists where the apparent RMS surface roughness and the speckle contrast exhibit a one-one correspondence. In addition, a speckle statistic other than speckle contrast may be used, as long as an operating range exists where the apparent RMS surface roughness and the statistic exhibit a one-one correspondence. In practice, the relationship is implemented as a look-up table, which may be determined in advance in a factory calibration procedure, and stored in a memory such as memory 107.

Now define a new random variable $\hat{h}$ by:

$$\hat{h} = h + \frac{l}{\eta \cos \theta} \quad (4)$$

Then it is clear that the standard deviation of this new random variable is the apparent RMS surface roughness, which is a parameter that can be calculated for each of the multiple speckle patterns by calculating the respective speckle contrast of the multiple speckle patterns for the multiple incident angles, and determining the respective apparent RMS surface roughness via table look-up. The mean path l is a random variable following the negative exponential distribution $f(l) = \sigma_t \exp(-\sigma_t l)$ with mean free path $\bar{l} = \sigma_t^{-1}$ and variance $\text{Var}(l) = \sigma_t^{-2}$, where $\sigma_t$ is the extinction coefficient, a parameter characteristic of the material.

From Equation 4, the apparent RMS surface roughness $\hat{\sigma}_h = \sigma_{\hat{h}}$ is related to the true RMS surface roughness $\sigma_h$ and material parameters $\sigma_t$ and η by the following:

$$\hat{\sigma}_h^2 \cos \theta = \sigma_h^2 \cos \theta + \frac{1}{\eta \sigma_t^2} \quad (5)$$

Thus, Equation 5 is a model which defines relatedness amongst all of apparent surface roughness, surface roughness, the sub-surface scattering property, and the incident angle, where the apparent surface roughness is $\hat{\sigma}_h$, the surface roughness is $\sigma_h$, the sub-surface scattering property is the combination of material parameters $\eta \sigma_t^2$, and the incident angle is θ.

To use the model defined by Equation 5, multiple speckle patterns are recorded using an apparatus as depicted in FIGS. 1A, B and C for multiple incident angles. For each incident angle θ, a speckle statistic, such as speckle contrast, is calculated. An apparent surface roughness, such as apparent RMS surface roughness $\hat{\sigma}_h$, is determined by a look up from a look-up table stored in memory 107, for example.

Thus, according to the above, a speckle statistic is calculated for each of the multiple speckle patterns. A numeric value for a parameter such as apparent surface roughness is determined for each of the calculated speckle statistics. The apparent surface roughness differs from surface roughness at least in part due to sub-surface scattering, as can be seen by comparing Equations 2 and 3.

Figure 7:
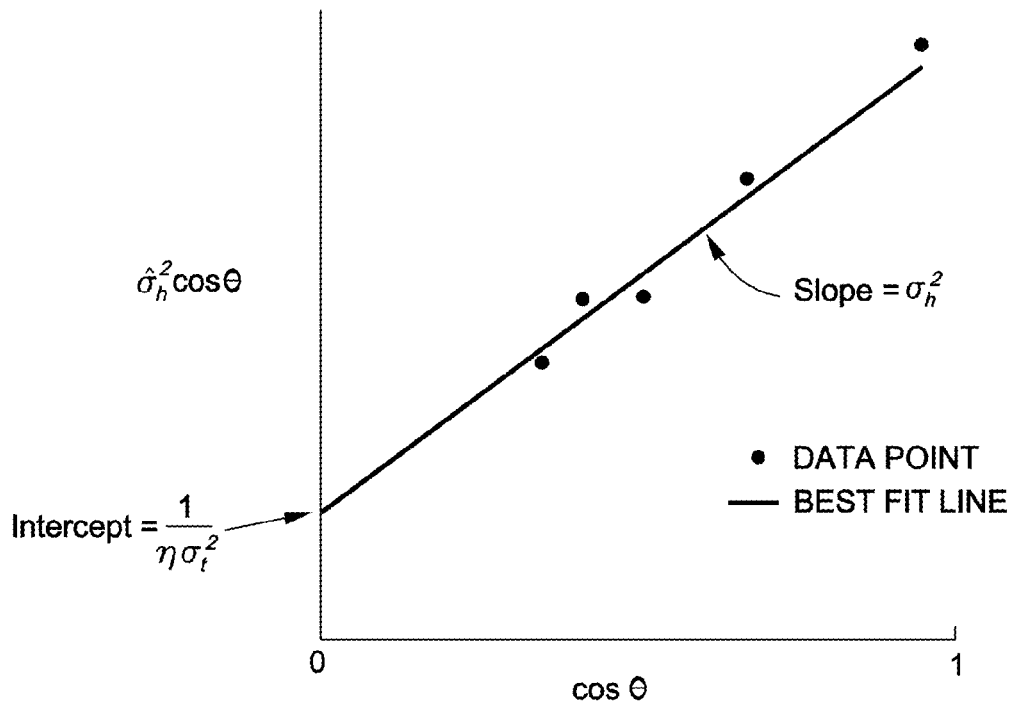
FIG. 7 is a view for explaining model fitting according to an example embodiment.

Equation 5 is used as a model for fitting the numeric values for apparent surface roughness and the incident angle. In one example embodiment, the fitting is done by a linear regression analysis. More specifically, a straight line is fitted for data points with ordinates $\hat{\sigma}_h^2 \cos \theta$ and abscissae $\cos \theta$, an illustrative view of which is shown in FIG. 7. The slope of the line of best fit gives $\sigma_h^2$ and therefore $\sigma_h$, while the vertical intercept of the line of best fit gives $1/(\eta \sigma_t^2)$, which is a combination of material parameters representative of the sub-surface scattering property. Thus, in this example, both of the surface roughness value and the sub-surface scattering property of the material are estimated by fitting the numeric values for apparent surface roughness to a model defining relatedness amongst all of apparent surface roughness, surface roughness, the sub-surface scattering property, and the incident angle. The sub-surface scattering property includes an extinction coefficient, the fitting is done by a regression analysis, and both of the surface roughness and the sub-surface scattering property are estimated from the fitted model. Accordingly, in this example, the sub-surface scattering property comprises an extinction coefficient, the model is fit using linear regression, and both of the surface roughness and the sub-surface scattering property (combination of the extinction coefficient and the relative refractive index) are estimated from the fitted model. In this manner, the true RMS roughness $\sigma_h$ and a combination of material parameters, $\eta\sigma_t^2$, can be determined simultaneously. If the relative refractive index $\eta$ is known, then the extinction coefficient $\sigma_t$ can be determined.

Thus, for each of the multiple speckle patterns, a numeric value for a parameter such as an apparent surface roughness is calculated, and the numeric values for the parameter are fit to a model. The model defines relatedness amongst all of the parameter, surface roughness, the sub-surface scattering property, and the incident angle. Both of the surface roughness value and the sub-surface scattering property of the material are estimated from the fitted model.

A different model other than the one given by Equation 5 may be used. For example, multiple scattering within the material may be considered instead of a single scattering. In the case of n scatterings within the material, where n is greater than one, the scattering path may not be symmetric about the surface normal direction. Instead of one random variable l for the free path, multiple independent random variables $l_0, l_1, \ldots, l_n$ may be used in the modeling. Other measures of surface roughness may be used in the model other than RMS surface roughness $\sigma_h$ (also denoted $R_q$), such as the average of absolute values $R_a$ or other measures. Similarly, other measures of apparent surface roughness may be used in the model other than RMS apparent surface roughness, such as the average of absolute values or other measures. Other material parameters other than relative refractive index and the extinction coefficient may appear in the model, such as a scattering coefficient, a reduced extinction coefficient, an effective extinction coefficient, an albedo parameter, a mean cosine of the scattering angle, a phase function or the like.

Other model fitting approaches can be used other than linear regression. More generally, an analysis of light scattering may result in a model of the following form, of which Equation 5 is a special case:

$$F(\theta, \sigma_h, \hat{\sigma}_h, \eta, \sigma_t, \ldots) = 0 \qquad (6)$$

where F is a nonlinear function. Model fitting may involve nonlinear regression. It may involve solving a nonlinear optimization problem, such as the following:

$$\sigma_h, \eta, \sigma_t, \ldots = \operatorname{argmin} \sum_{i=1}^{N} \Delta(F(\theta^i, \sigma_h, \hat{\sigma}_h^i, \eta, \sigma_t, \ldots)) \qquad (7)$$

where $\hat{\sigma}_h^i$ corresponds to the apparent surface roughness for the ith incident angle $\theta^i$, N is the number of data points, which is also the number of incident angles used in the material property estimation, and $\Delta$ is an error metric for evaluating the goodness of fit. For example, $\Delta(x)=x^P$ corresponding to minimizing the LP-norm fitting error. An objective function even more general than that depicted in Equation 7 may be used in a nonlinear optimization problem. The number of incident angles N used affects the quality of the estimates of the material properties. Generally, the larger the number of incident angles used, the higher is the quality of the estimates. For a model defined by Equation 5 which can be considered a linear model with the choice of ordinate $\hat{\sigma}_h^2 \cos\theta$ and abscissa $\cos\theta$, the number of incident angles should be at least three, i.e., N≥3. In general, for a nonlinear model, more incident angles should be used for higher quality of the estimates of the material properties.

Referring to FIG. 4, after step 403, the estimates of surface roughness and sub-surface scattering properties may be used in the classification, discrimination and identification of materials. In one example, the material is comprised of skin tissue, and the estimate of surface roughness is used as a non-invasive method to evaluate skin properties such as malignancy of skin lesion. In another example, the material is comprised of a recyclable material such as plastic bottles, and the estimate of sub-surface scattering property is used to classify different types of plastics such as PET (polyethylene terephthalate).

<Other Embodiments>

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a function expansion unit removably inserted in and/or remotely accessed by the apparatus or system for use with the computer processor(s).

This disclosure has provided a detailed description with respect to particular representative embodiments. It is understood that the scope of the appended claims is not limited to the above-described embodiments and that various changes and modifications may be made without departing from the scope of the claims.

What is claimed is:

1. A method of estimating both of a surface roughness value and a sub-surface scattering property of a material, the method comprising:
    illuminating the material with a light beam with controlled coherence properties at multiple incident angles;
    recording multiple speckle patterns, each speckle pattern being recorded for a respective one of the multiple incident angles; and
    estimating both of a surface roughness value and a sub-surface scattering property of the material by calculations using the multiple speckle patterns and the incident angle for each such speckle pattern,
    wherein the estimating step comprises:
    calculating, for each of the multiple speckle patterns, a numeric value for a parameter;
    fitting the numeric values to a model, wherein the model defines relatedness amongst all of the parameter, surface roughness, the sub-surface scattering property, and the incident angle; and
    estimating both of the surface roughness value and the sub-surface scattering property of the material from the fitted model.

2. The method according to claim 1, wherein the method further comprises:
    calculating for each of the multiple speckle patterns, a speckle statistic;
    determining a numeric value for apparent surface roughness for each of the calculated speckle statistics, wherein the apparent surface roughness differs from surface roughness at least in part due to sub-surface scattering; and
    estimating both of the surface roughness value and the sub-surface scattering property of the material by fitting the numeric values for apparent surface roughness to a model defining relatedness amongst all of apparent surface roughness, surface roughness, the sub-surface scattering property, and the incident angle.

3. The method according to claim 2, wherein the sub-surface scattering property comprises an extinction coefficient, the fitting is done by a regression analysis, and both of the surface roughness and the sub-surface scattering property are estimated from the fitted model.

4. The method according to claim 3, wherein the model defines relatedness as follows:

$$\hat{\sigma}_h^2 \cos\theta = \sigma_h^2 \cos\theta + \frac{1}{\eta \sigma_t^2}$$

wherein $\hat{\sigma}_h$ is the apparent surface roughness, $\sigma_h$ is the surface roughness, $\theta$ is the incident angle, $\eta$ is the refractive index of the material, and $\sigma_t$ is the extinction coefficient.

5. The method according to claim 1, wherein the sub-surface scattering property comprises at least one material property selected from the group consisting of absorption coefficient, scattering coefficient and extinction coefficient.

6. The method according to claim 1, wherein the material is comprised of skin tissue.

7. The method according to claim 1, wherein the material is comprised of a recyclable material.

8. An apparatus for estimating both of a surface roughness value and a sub-surface scattering property of a material, comprising:
    a computer-readable memory constructed to store computer-executable process steps; and
    a processor constructed to execute the computer-executable process steps stored in the memory;
    wherein the process steps stored in the memory cause the processor to:
    illuminate the material with a light beam with controlled coherence properties at multiple incident angles;
    record multiple speckle patterns, each speckle pattern being recorded for a respective one of the multiple incident angles; and
    estimate both of a surface roughness value and a sub-surface scattering property of the material by calculations using the multiple speckle patterns and the incident angle for each such speckle pattern,
    wherein the estimating comprises:
    calculating, for each of the multiple speckle patterns, a numeric value for a parameter;
    fitting the numeric values to a model, wherein the model defines relatedness amongst all of the parameter, surface roughness, the sub-surface scattering property, and the incident angle; and
    estimating both of the surface roughness value and the sub-surface scattering property of the material from the fitted model.

9. The apparatus according to claim 8, wherein the process steps further cause the processor to:
    calculate for each of the multiple speckle patterns, a speckle statistic;
    determine a numeric value for apparent surface roughness for each of the calculated speckle statistics, wherein the apparent surface roughness differs from surface roughness at least in part due to sub-surface scattering; and
    estimate both of the surface roughness value and the sub-surface scattering property of the material by fitting the numeric values for apparent surface roughness to a model defining relatedness amongst all of apparent surface roughness, surface roughness, the sub-surface scattering property, and the incident angle.

10. The apparatus according to claim 9, wherein the sub-surface scattering property comprises an extinction coefficient, the fitting is done by a regression analysis, and both of the surface roughness and the sub-surface scattering property are estimated from the fitted model.

11. The apparatus according to claim 10, wherein the model defines relatedness as follows:

$$\hat{\sigma}_h^2 \cos\theta = \sigma_h^2 \cos\theta + \frac{1}{\eta \sigma_t^2}$$

wherein $\hat{\sigma}_h$ is the apparent surface roughness, $\sigma_h$ h is the surface roughness, $\theta$ is the incident angle, $\eta$ is the refractive index of the material, and $\sigma_t$ is the extinction coefficient.

12. The apparatus according to claim 8, wherein the sub-surface scattering property comprises at least one material property selected from the group consisting of absorption coefficient, scattering coefficient and extinction coefficient.

13. The apparatus according to claim 8, wherein the material is comprised of skin tissue.

14. The apparatus according to claim 8, wherein the material is comprised of a recyclable material.

15. A non-transitory computer-readable storage medium on which is stored computer-executable process steps for causing a computer to perform a method for estimating both of a surface roughness value and a sub-surface scattering property of a material, the method comprising:
   illuminating the material with a light beam with controlled coherence properties at multiple incident angles;
   recording multiple speckle patterns, each speckle pattern being recorded for a respective one of the multiple incident angles; and
   estimating both of a surface roughness value and a sub-surface scattering property of the material by calculations using the multiple speckle patterns and the incident angle for each such speckle pattern,
   wherein the estimating step comprises:
   calculating, for each of the multiple speckle patterns, a numeric value for a parameter;
   fitting the numeric values to a model, wherein the model defines relatedness amongst all of the parameter, surface roughness, the sub-surface scattering property, and the incident angle; and
   estimating both of the surface roughness value and the sub-surface scattering property of the material from the fitted model.

16. The storage medium according to claim 15, wherein the method further comprises:
   calculating for each of the multiple speckle patterns, a speckle statistic;
   determining a numeric value for apparent surface roughness for each of the calculated speckle statistics, wherein the apparent surface roughness differs from surface roughness at least in part due to sub-surface scattering; and
   estimating both of the surface roughness value and the sub-surface scattering property of the material by fitting the numeric values for apparent surface roughness to a model defining relatedness amongst all of apparent surface roughness, surface roughness, the sub-surface scattering property, and the incident angle.

17. The storage medium according to claim 16, wherein the sub-surface scattering property comprises an extinction coefficient, the fitting is done by a regression analysis, and both of the surface roughness and the sub-surface scattering property are estimated from the fitted model.

* * * * *